(12) United States Patent
Ding

(10) Patent No.: US 8,079,977 B2
(45) Date of Patent: Dec. 20, 2011

(54) POWDER AUTOMATIC MIXING APPARATUS

(75) Inventor: Yuying Ding, Beijing (CN)

(73) Assignee: Wei Zhang, Xiamen (CN)

( * ) Notice: Subject to any disclaimer, the term of this patent is extended or adjusted under 35 U.S.C. 154(b) by 202 days.

(21) Appl. No.: 12/526,823

(22) PCT Filed: Feb. 2, 2008

(86) PCT No.: PCT/CN2008/000266
§ 371 (c)(1),
(2), (4) Date: Aug. 12, 2009

(87) PCT Pub. No.: WO2008/101393
PCT Pub. Date: Aug. 28, 2008

(65) Prior Publication Data
US 2010/0286606 A1    Nov. 11, 2010

(30) Foreign Application Priority Data
Feb. 14, 2007  (CN) .......................... 2007 1 0008629

(51) Int. Cl.
*A61M 37/00*   (2006.01)
(52) U.S. Cl. ........................................................ 604/92
(58) Field of Classification Search ................ 604/82, 604/85, 86, 87, 88, 92, 191, 192
See application file for complete search history.

(56) References Cited

U.S. PATENT DOCUMENTS

| 4,227,528 A | * | 10/1980 | Wardlaw ..................... 604/139 |
| 4,861,335 A | * | 8/1989 | Reynolds ....................... 604/88 |
| 5,171,220 A | | 12/1992 | Morimoto |
| 5,876,372 A | | 3/1999 | Grabenkort et al. |

FOREIGN PATENT DOCUMENTS

| CN | 2748094 Y | 12/2005 |
| CN | 1772313 A | 5/2006 |
| JP | 2000316973 A | 11/2000 |
| WO | WO-8802265 A1 | 4/1988 |

* cited by examiner

*Primary Examiner* — Christopher D Koharski
(74) *Attorney, Agent, or Firm* — Rabin & Berdo, P.C.

(57) ABSTRACT

A device for automatically mixing powder for injection, includes an injector body, a solvent bottle, a needle, a first impelling unit and a second impelling unit. The injector body has a solute bottle and its mouth is opposite the mouth of the solvent bottle. The first impelling unit is disposed upon the solvent bottle. The second impelling unit is sleeved with a needle and located between the mouth of solute bottle and mouth of solvent bottle. A first and a second impelling sleeve-are driven by the solvent bottle to slide along the solute bottle, so the first end of the needle is fixed and extend through the solute bottle. The solvent bottle drives the first impelling sleeve and second impelling sleeve to turn with each other. The second impelling sleeve slides opposite the first impelling sleeve to make the second end of the needle extend through the solvent bottle.

10 Claims, 5 Drawing Sheets

POWDER AUTOMATIC MIXING APPARATUS

TECHNICAL FIELD

The present invention relates to an injector, especially relates to a device for automatically mixing powder for injection.

BACKGROUND OF THE INVENTION

The present inventor applied for a Chinese invention patent titled an injector for automatically mixing powder for injection on Sep. 14, 2005, and its publication date is May 17, 2006. An injector for automatically mixing powder for injection, comprising a solvent bottle, a solute bottle, a needle cap, a solute bottle sleeve, a solvent bottle sleeve, a turntable sleeve, first impelling sleeve and second impelling sleeve, said solute bottle is set inside said solvent bottle sleeve, said solvent bottle, the first and second impelling sleeve are set inside said solvent bottle sleeve, said turntable sleeve is sleeved outside said solvent bottle sleeve, and said solute bottle sleeve and solvent bottle sleeve are connected together in a up and down position. The turntable sleeve drives said first and second impelling sleeve to move along the first impelling and second impelling restrict slot respectively, then the needle of said needle cap firstly penetrate the glue tampon of said solute bottle and locate therein, then penetrate the glue tampon of said solvent bottle, the solvent in the solvent bottle flow into said solute bottle under the pressure, so the powder for injection can be mixed automatically. There are a first impelling restrict slot, second impelling restrict slot and a location card of said turntable sleeve reside at the inner wall of said turntable sleeve, the strike line of said first and second restrict slot is of spiral shape or may be an arc with certain angle. However, there are some drawbacks in the above technology: firstly, the manufacturing process may be complex and costs a lot, because it requires a high precession when making the spiral shape or an arc with certain angle of the first and second restrict slot at the inner wall of turntable sleeve; secondly, the structure of said injector is complex and may be difficult to assemble because too many sleeves are needed, including solute bottle, solvent bottle and turntable bottle.

SUMMARY OF THE INVENTION

The present invention provides a device for automatically mixing powder for injection, which overcome the drawbacks of the background invention such as complex manufacturing process, a high cost, complex structure, and inconvenient to assemble.

The technical solution applied in the present invention is: a device for automatically mixing powder for injection, comprising a injector body, a solvent bottle, a needle, first and second impelling unit, said injector body has a solute bottle and its mouth is opposite the mouth of solvent bottle; said first impelling unit is disposed upon the solvent bottle for driving said solvent slide along said solute bottle; said second impelling unit sleeve with a needle and locate between said mouth of solute bottle and mouth of solvent bottle, further comprising a first impelling sleeve and a second impelling sleeve; wherein, said first and second impelling sleeve are driven by the solvent bottle and then slide along said solute bottle, so the first end of said needle is fixed and extend through said solute bottle, said solvent bottle further drive said first impelling sleeve and said second impelling sleeve to turn with each other, then the second impelling sleeve slide along the first impelling sleeve to make the second end of said needle extend through said solvent bottle.

The bottom surface of said second impelling sleeve is downwardly protruded and disposed with a falling part; the top surface of said first impelling sleeve is upwardly protrude and disposed with a deflecting part, moreover, said top surface is downwardly concave and has a sudden-drop slot for containing said falling part; wherein, said falling part cooperate with the deflecting part to form a deflecting unit which can switch from mutually sliding movement to mutually turning movement, said falling part lean upon said deflecting part, or may be turn with each other than fall to said sudden-drop slot so as to make said second impelling sleeve slide opposite said first impelling sleeve.

Said first impelling unit comprising an elastic body and a switch, said switch control said elastic body to release elastic force, said elastic force drive said solvent bottle to slide along said solute bottle.

The outside of said solvent bottle is sleeved with a solvent bottle sleeve, and the inside of said solvent bottle sleeve is slidably arranged with a spring sleeve which is located upon said solvent bottle, said top of said spring sleeve has a fastening plate; said switch comprising a lock connection slot set on the fastening plate and a pushing stick which extends through said spring sleeve, the bottom side of said pushing stick lean upon said solvent bottle, moreover, the top of said pushing stick is concave inwardly and has a switch slot, the bottom of said pushing stick is protrude outwardly and has protruding ring, said elastic body is sleeved with said pushing stick and locate between said the protruding ring and the fastening plate; wherein, said switch slot is embedded into said lock connection slot of said spring sleeve for energy storage, the turning of said pushing stick can cause the switch slot to depart from said lock connection slot and then release the elastic energy of elastic body.

said switch further comprising a knob, said knob connect with the top of pushing stick but can not turn around mutually; the bottom surface of said knob has a convex top incline, the top surface of said spring sleeve has a convex bottom incline, wherein, said top incline of the knob is fitted and lean upon the bottom incline of said spring sleeve.

The top of the outer sleeve of said solvent bottle is removable connect to said solvent bottle sleeve cover; the top of said knob is turntable get through said sleeve cover, and the bottom of said knob is turntable set beneath said solvent bottle sleeve cover.

Said second impelling sleeve is slidably connect to the inside of said solvent bottle sleeve, said first impelling sleeve is connected to the inside of said solvent bottle sleeve which can firstly slide along said solvent bottle and then turn with it.

Said sudden-drop slot is connected adjacent said deflecting part.

There is mouth disposed on the solvent bottle sleeve for observing if the solvent is totally injected to the solute bottle or not.

Said solvent bottle is a clip type bottle, further comprising a sealable pushing tampon slidably set inside said solvent bottle; the bottom surface of said spring sleeve is set adjacent the top side of said clip type bottle, said pushing stick is set adjacent the top surface of said pushing tampon.

The automatically mixing powder for injection device applied in the present technical solution, wherein the mixing of powder for injection can be finished by only sliding the solvent bottle along the solute bottle, so its operation is convenient, efficient and safe, moreover, since the present invention do not need many sleeves and do not need to set the spiral shape slot or the arc slot with certain angle, thus, the structure would be simple, and the manufacturing process and assembly is easy and of low cost. The arrangement of elastic body can automatically press the solvent in said solvent bottle into the solute bottle by the elastic force, it needn't restrict the relative position of said solvent bottle and solute bottle during the operation process, furthermore, the solvent in said solvent bottle can be fully utilized. The slidable connection between the second impelling sleeve and the inside of solvent bottle, and the first impelling sleeve and the inside of solvent bottle can firstly slide mutually and then turn mutually, it can ensure the needle sequentially go through said solute bottle and solvent bottle, so the operation is convenient and safe.

BRIEF DESCRIPTION OF THE DRAWINGS

The present invention can be understood by referring to the following accompanying drawings and the detailed description of the preferred embodiments, wherein:

FIG. 2 and FIG. 3 are adapted to form a complete sectional view of a device for automatically mixing powder for injection.

Figure 1:
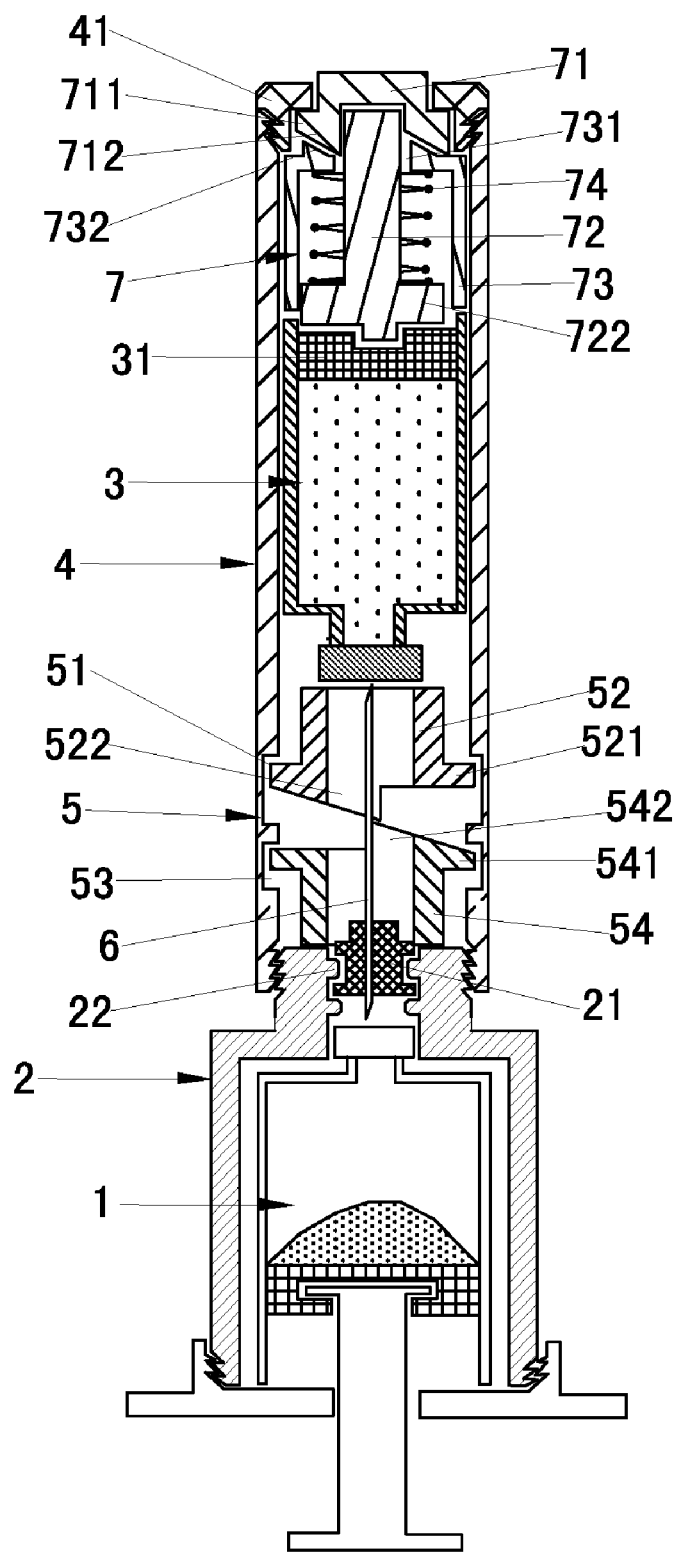
FIG. 1 shows a sectional view of a device for automatically mixing powder for injection of the present invention.

DIAGRAM LEGEND solute bottle 1, solute bottle sleeve 2, solvent bottle 3, solvent bottle sleeve 4, second impelling unit 5, needle 6, first impelling unit 7, needle cap 21, stuck point of needle cap 22, pushing tampon 31, sleeve cover 41, first connection slot 51, first impelling sleeve 52, second connection slot 53, second impelling sleeve 54, knob 71, pushing stick 72, spring sleeve 73, elastic body 74, first axial sliding slot 511, first lateral sliding slot 512, first protruding block 521, deflecting part 522, sudden-drop slot 523, second protruding block 541, falling part 542, leaning part 711, top incline 712, switch slot 721, protruding ring 722, lock connection slot 731 and bottom incline 732.

DETAILED DESCRIPTION OF EMBODIMENTS

Figure 2:
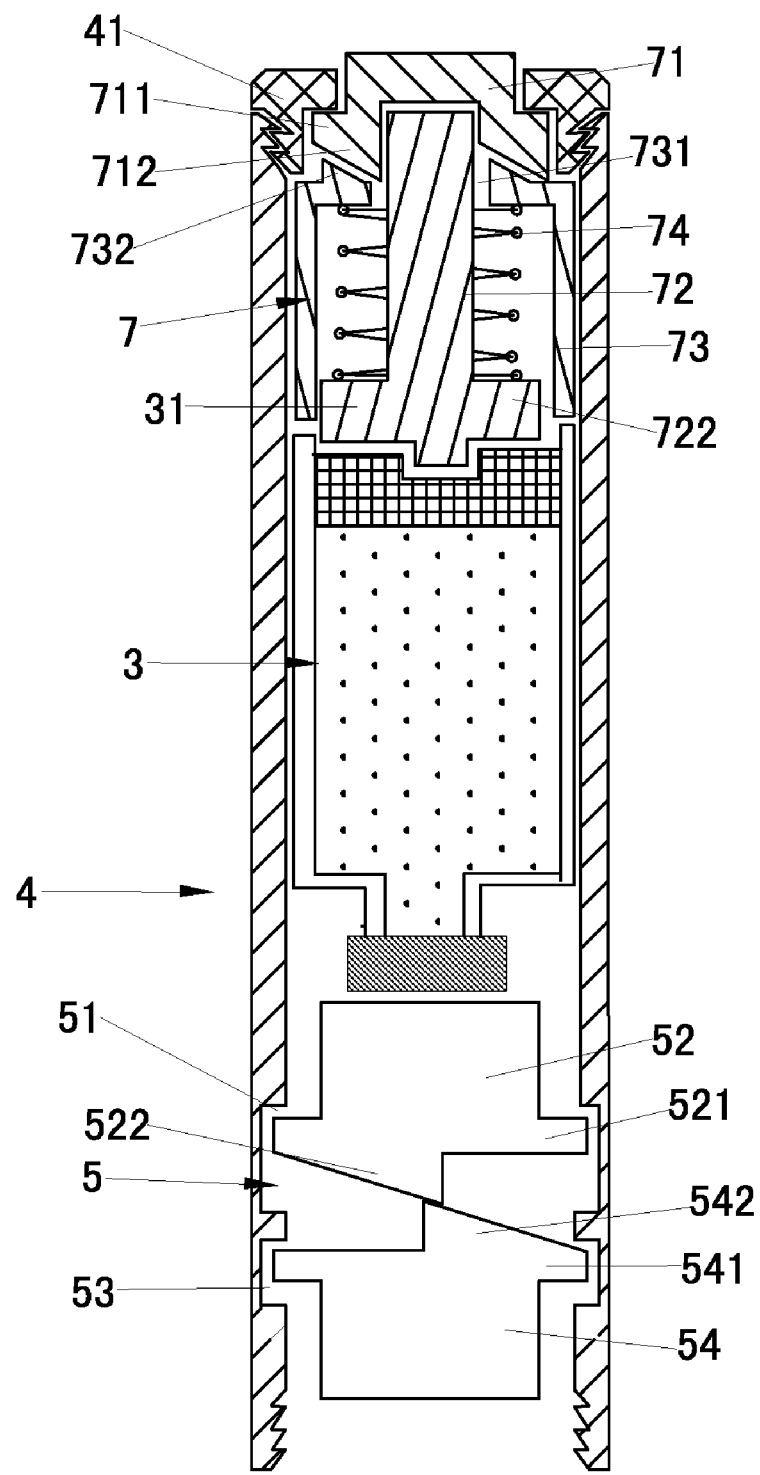
FIG. 2 shows the solvent bottle, sleeve and other structure of a device for automatically mixing powder for injection of the present invention.
Figure 3:
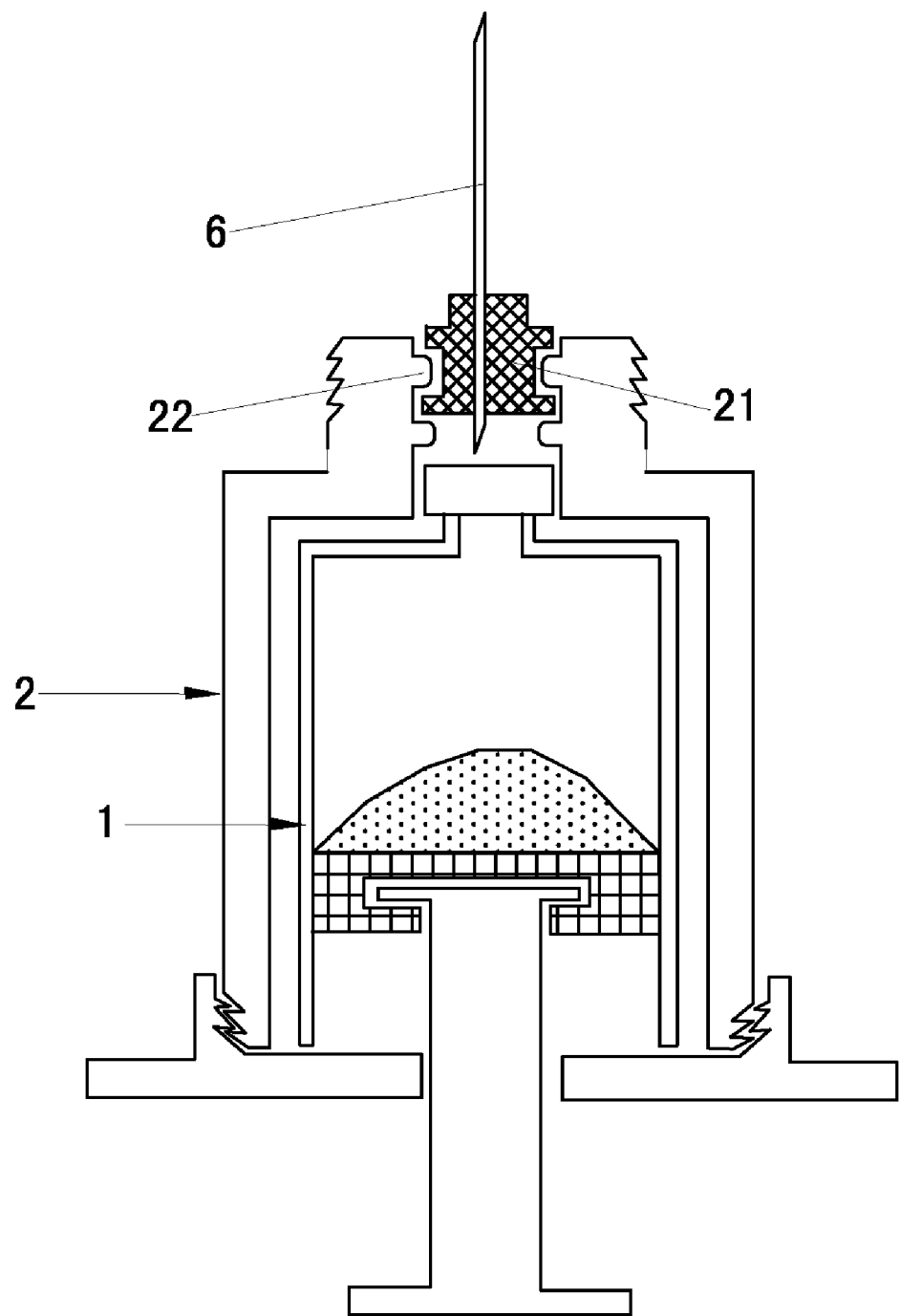
FIG. 3 shows the injector body, needle and other structure of a device for automatically mixing powder for injection of the present invention.

A device for automatically mixing powder for injection, please refer to FIG. 1, FIG. 2 and FIG. 3, which comprising a injector body, a solvent bottle 3, a solvent bottle sleeve 4, a first impelling unit 7, second impelling unit 5 and needle 6. Said injector body cooperate with needle 6 to form an injector, which comprising a solute bottle 1, a solute bottle sleeve 2 and other parts. Said solvent bottle 3 is of clip type, that is no base, furthermore there is a sealable pushing tampon 31 slidably connected inside of said solvent bottle 3.

Please refer to FIG. 3, the solute bottle sleeve 2 is ladder shape and its top part is relatively smaller than its bottom part, the top side of the sleeve is configured as a first screw socket, furthermore there are two stuck points 22 of needle cap disposed in the sleeve, said stuck point has needle cap 21, said needle 6 is fastened to needle cap 21.

Please refer to FIG. 1 and FIG. 2, the bottom side of said solvent bottle sleeve 4 is configured as the second screw socket, said second screw socket is screw jointed with the first screw socket of solute bottle sleeve 2, so that the solute bottle sleeve 2 and solvent bottle sleeve 4 can be removable connected, that is, the injector body and solvent bottle sleeve 4 can be removable connected. If it is necessary, there may further has a mouth disposed on the solvent bottle sleeve 4 for observing if the solvent of the solvent bottle 3 is totally injected into the solute bottle 1 or not.

Please refer to FIG. 1, FIG. 2 and FIG. 3, the solvent bottle sleeve 4 is sleeved with said solute bottle 3, and the mouth of solute bottle 1 is opposite the mouth of solvent bottle 3. The second impelling unit 5 is set between the mouth of solute bottle 1 and the mouth of solvent bottle 3, said second impelling unit 5 comprising a first connection slot 51, a first impelling sleeve 52, a second connection slot 53 and a second impelling sleeve 54.

Figure 6:
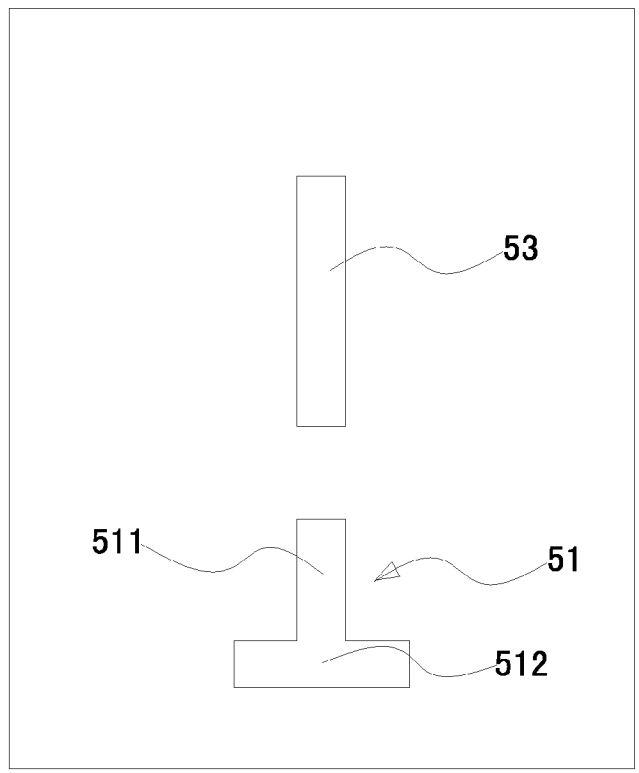
FIG. 6 shows the principle of the connection slot set at the sleeve of a device for automatically mixing powder for injection of the present invention.

Please refer to FIG. 6, the first connection slot 51 is set at the inner wall of sleeve 4, comprising a first axial sliding slot 511 and two first lateral sliding slots 512, said lateral sliding slot 512 get through the bottom mouth of said first axial sliding slot 511. The second connection slot 53 is set at the inner wall of sleeve 4, and further comprising two first axial sliding slots.

Figure 4:
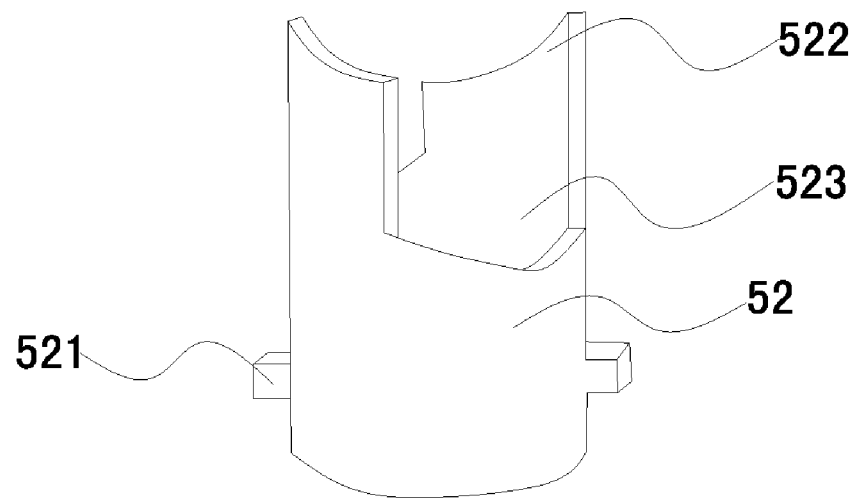
FIG. 4 shows a vertical view of the first impelling sleeve of a device for automatically mixing powder for injection of the present invention.

Please refer to FIG. 4, the first impelling sleeve 52 has two first protruding blocks 521 oppositely set outside thereof, said two first protruding blocks are slidably connected to said two first connection slots 51 respectively, so that said first impelling sleeve 52 is connected to the inside of said solvent bottle sleeve 4 which can firstly slide along said solvent bottle and then turn with each other. The top surface of said first impelling sleeve 52 is outwardly protrude and disposed with a spiral shaped deflecting part 522, moreover, said top surface of the first impelling sleeve 52 is downwardly concave and has a sudden-drop slot 523, said sudden-drop slot 523 is connected adjacent the deflecting part 522.

Figure 5:
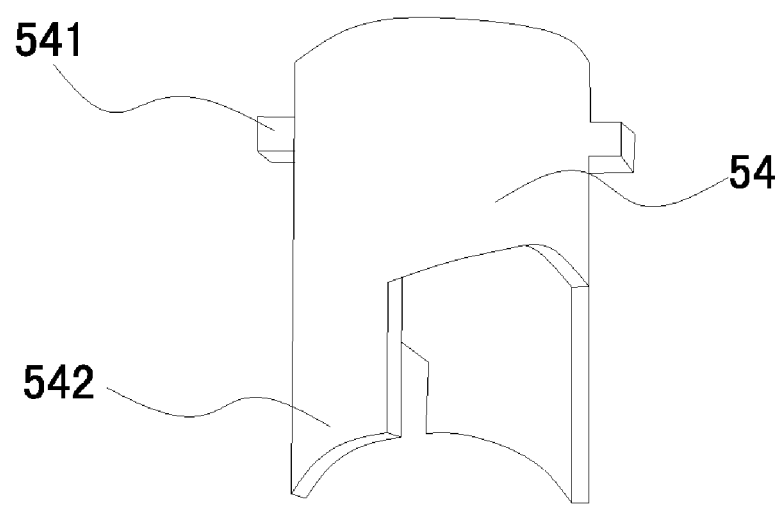
FIG. 5 shows a vertical view of the second impelling sleeve of a device for automatically mixing powder for injection of the present invention.

Please refer to FIG. 5, the second impelling sleeve 54 has two second protruding block 541 oppositely set outside thereof, said two second protruding block 541 is slidably connected to the second connection slot 53 (the second axial sliding slot) respectively, so that said second impelling sleeve 54 and solvent bottle sleeve 4 can be slidably connected. The bottom surface of said second impelling sleeve 54 is downwardly protruded and disposed with a spiral shaped falling part 542.

Please refer to FIG. 1 and FIG. 2, the first impelling sleeve 52 and second impelling sleeve 54 are sleeved inside the solvent bottle sleeve 4, said first impelling sleeve 52 lean upon the needle cap 21, said second impelling sleeve 54 lean beneath the mouth of solvent bottle 3. Said falling part 542 and deflecting part 522 form a deflecting unit and can switch from mutually sliding movement to mutually turning movement. When no powder for injection mixed or at the early stage of mixing (to better understand please refer to the following mixing steps), said falling part 542 lean upon said deflecting part 522, during the mixing process, when said second impelling sleeve 54 do a turning movement but unslidable, the deflecting unit start to work, after said falling part 542 and deflecting part 522 turning with each other, the falling part 542 fall into sudden-drop slot 523, the second impelling sleeve 54 slide along the first impelling sleeve 52.

Please refer to FIG. 1 and FIG. 2, the needle 6 is set between the mouth of solute bottle and the mouth of solvent bottle, and slidably goes through said first and second impelling sleeve 52, 54.

Please refer to FIG. 1 and FIG. 2, the top side of solvent bottle sleeve 4 is disposed with a removable sleeve cover 41. Said first impelling unit 7 is set upon the pushing tampon 31 of solvent bottle 3, comprising a knob 71, a pushing stick 72, a spring sleeve 73 and an elastic body 74.

Please refer to FIG. 1 and FIG. 2, the knob 71 is outwardly protrude and disposed with a leaning part 711, and its bottom surface is a convex top incline 712. Said knob 71 is sleeved inside the solvent bottle sleeve 4, its top part get through said sleeve cover 41 downwardly, and the leaning part 711 lean beneath the bottom surface of sleeve cover 41, so that said knob 71 can turn with sleeve cover 41 mutually, moreover it prevent the knob 71 from separating from sleeve cover 41.

Figures 7, 8:
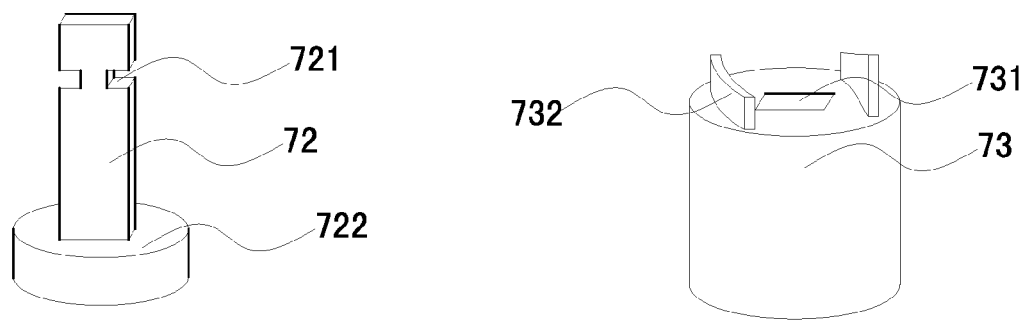
FIG. 7 shows the vertical view of the pushing stick of a device for automatically mixing powder for injection of the present invention.
FIG. 8 shows the vertical view of the spring sleeve of a device for automatically mixing powder for injection of the present invention.

Please refer to FIG. 1, FIG. 2 and FIG. 7, the cross section of the body of pushing stick 72 is rectangle, the upper middle part of the pushing stick is disposed with a switch slot 721 inwardly, the bottom part of the pushing stick is outwardly convex and configured as a protruding ring 722, its bottom side lean upon the pushing tampon of solvent bottle 3. And the top side lean upon the tampon of solvent bottle 3. The top part of said pushing stick 72 is connected to knob 71 but can not turn with each other.

Please refer to FIG. 1, FIG. 2 and FIG. 8, the top side of spring sleeve is disposed with a fastening plate, the top surface of said fastening plate is convex and disposed with a bottom incline 732, said top incline 712 is fitted and leaned upon said bottom incline 732. Said fastening plate further set with rectangle lock connection slot 731, said pushing stick 72 goes through spring sleeve 73 and its bottom side goes through said lock connection slot 731.

Please refer to FIG. 1, FIG. 2, the elastic body 74 sleeve with pushing stick 72 and between protruding ring 722 and the fastening plate of spring sleeve 73; the switch slot 721 of said pushing stick 72 is embedded into said lock connection slot 731 of said spring sleeve 73 for energy storage, the turning of said pushing stick 72 can drive the switch slot 721 to depart from said lock connection slot 731 and then release the elastic energy of elastic body 74. Said switch slot 721 cooperate with lock connection 731 to form a switch. The bottom surface of spring sleeve lean the bottom side of clip type bottle, and the pushing stick lean the top surface of pushing tampon.

The mixing steps of the mixing device are as below:

P1. Turning around the knob 71, then the top incline 712 of knob 71 cooperates with the bottom incline 732 of the spring sleeve 73 to make the spring sleeve 73 has a pushing force, said pushing force push against said solvent bottle 3 (clip type bottle) to slide downwardly (along the solute bottle 1), meanwhile when said knob 71 turn to a certain angle, the length of the rectangle cross section of pushing stick 72 is parallel to that of lock connection slot 731, then the switch slot 721 depart from the lock connection slot 731 of spring sleeve 73, so the elastic body 74 release the elastic energy to generate elastic force, said elastic force drive the pushing stick 72 to slide downwardly, and the pushing stick 72 push the pushing tampon 31 to slide downwardly along the clip type bottle relatively, so the inside of clip type bottle can acquire a high atmospheric pressure, when the atmospheric pressure rise to a certain high degree, said elastic force push the pushing tampon 3 and said clip type bottle slide downwardly, under the influence of said first axial sliding slot 511 and second axial sliding slot [微软用户1], then the first and the second impelling sleeve 52, 54 slide downwardly too, said first impelling sleeve 52 press the needle cap 21 which is set upon the stuck point 22, so the needle cap 21 is embedded into the stuck point 22 of the injector body, furthermore, the bottom side of the needle 6 is caused to penetrate the tampon of said solute bottle 1 so as to get through the solute bottle 1;

P2. When the first impelling sleeve 52 slide to the first lateral sliding slot 512, continue turning the knob 71 to cause the solvent bottle to slide downwardly (slide along the solute bottle continuously), under the influence of the deflecting unit, the first impelling sleeve 52 and second impelling sleeve 54 turn with each other, then the falling part 542 fall into the sudden-drop slot 523, the second impelling sleeve 54 slide downwardly opposite the first impelling sleeve 52, then the solvent bottle 3 move downwardly to cause the top of needle 6 to penetrate the tampon of the solvent bottle 3 to get through the solvent bottle 3, meanwhile the elastic body push the pushing tampon 31, so that the solvent in the solvent bottle is injected into the solute bottle.

P3. Removing the injector body from said solvent bottle sleeve 4, said injector body has a needle, thus it is a complete injector.

To better understand the other structures of the present invention, please refer to the application titled a device for automatically mixing powder for injection which applied on Sep. 14, 2005.

Although the present invention has been described with reference to the preferred embodiments thereof and the best modes for carrying out the invention, it is apparent to those skilled in the art that a variety of modifications and changes may be made without departing from the scope of the present invention which is intended to be defined by the appended claims.

INDUSTRIAL APPLICABILITY

The present invention discloses a device for automatically mixing powder for injection, its operation is convenient, efficient and safe, moreover it has a simple structure, thus the manufacturing process thereof is easy, and of a low cost, which is applicable in industry.

The invention claimed is:

1. A device for automatically mixing powder for injection, comprising:
  an injector body including a solute bottle having a mouth;
  a solvent bottle having a mouth opposite to the mouth of the solute bottle;
  a needle;
  a first impelling unit disposed upon the solvent bottle for driving the solvent bottle to slide toward the solute bottle; and
  a second impelling unit which is sleeved with the needle therein and located between the mouth of the solute bottle and the mouth of the solvent bottle, the second impelling unit comprising:
  a first impelling sleeve having a downwardly concave top surface that is upwardly protruded and includes a deflecting part and a sudden-drop slot; and
  a second impelling sleeve having a bottom surface that is downwardly protruded and includes a falling part that is receivable within the sudden-drop slot, said first and second impelling sleeves being driven by the solvent bottle to slide relative to the solute bottle, so that a first end of the needle extends into the solute bottle, the solvent bottle further drives the first and said second impelling sleeves to turn relative to each other, the second impelling sleeve sliding along the first impelling sleeve to make a second end of the needle extend into the solvent bottle, the falling part cooperating with the deflecting part to form a deflecting unit which is switchable from a mutually sliding movement to a mutually turning movement, said falling part being pressable upon the deflecting part, and the falling part and the deflecting part being turnable relative to each other until the falling part falls into the sudden-drop slot, thereby causing the second impelling sleeve to slide opposite the first impelling sleeve.

2. A device for automatically mixing powder for injection according to claim 1, wherein:
said first impelling unit comprises an elastic body and a switch, said switch controlling said elastic body to release an elastic force, said elastic force driving said solvent bottle to slide toward said solute bottle.

3. A device for automatically mixing powder for injection according to claim 1, wherein:
an outside of said solvent bottle is sleeved with a solvent bottle sleeve, and an inside of said solvent bottle sleeve is slidably arranged with a spring sleeve which is located upon said solvent bottle, a top of said spring sleeve having a fastening plate;
said switch comprises a lock connection slot set on a fastening plate and a pushing stick which extends through the spring sleeve, a bottom side of said pushing stick pressing against said solvent bottle, a top of said pushing stick being inwardly concave and having a switch slot, a bottom of said pushing stick protruding outwardly and having a protruding ring, said elastic body being sleeved with said pushing stick and located between said protruding ring and said fastening plate;
wherein, said switch slot of said pushing stick is embedded into said lock connection slot for energy storage, a turning of said pushing stick causing the switch slot to depart from said lock connection slot to release an elastic energy of the elastic body.

4. A device for automatically mixing powder for injection according to claim 3, wherein: said switch further comprising a knob connected with the top of pushing stick so as to not be mutually turnable; a bottom surface of said knob having a convex top incline, a top surface of said spring sleeve having a convex bottom incline, wherein, the top incline of the knob is fitted and presses upon the bottom incline of said spring sleeve.

5. A device for automatically mixing powder for injection according to claim 4, wherein a top of the solvent bottle sleeve is removably connected to a solvent bottle sleeve cover; a top of said knob protrudes through said sleeve cover, and a bottom of said knob is turnable beneath said sleeve cover.

6. A device for automatically mixing powder for injection according to claim 3, wherein:
said second impelling sleeve is slidably connected to an inside of said solvent bottle sleeve, said first impelling sleeve is connected to the inside of said solvent bottle sleeve which is slidable along said solvent bottle and turnable with each other.

7. A device for automatically mixing powder for injection according to claim 1, wherein:
said sudden-drop slot is connected adjacent to said deflecting part.

8. A device for automatically mixing powder for injection according to claim 3, wherein:
the solvent bottle sleeve includes a mouth for observing if a solvent is totally injected into the solute bottle or not.

9. A device for automatically mixing powder for injection according to claim 4, wherein: said solvent bottle is a clip type bottle, further comprising a sealable pushing tampon slidably set inside said solvent bottle; a bottom surface of said spring sleeve being set adjacent a top side of said clip type bottle, said pushing stick being set adjacent a top surface of said pushing tampon.

10. A device for automatically mixing powder for injection, comprising:
an injector body including a solute bottle having a mouth;
a solvent bottle having a mouth opposite to the mouth of the solute bottle;
a needle;
a first impelling unit disposed upon the solvent bottle for driving the solvent bottle to slide toward the solute bottle; and
a second impelling unit which is sleeved with the needle therein and located between the mouth of the solute bottle and the mouth of the solvent bottle, the second impelling unit comprising:
a first impelling sleeve; and
a second impelling sleeve, said first and second impelling sleeves being driven by the solvent bottle to slide relative to the solute bottle, so that a first end of the needle fixed extends into the solute bottle, the solvent bottle further drives the first and said second impelling sleeves to turn relative to each other, the second impelling sleeve sliding along the first impelling sleeve to make a second end of the needle extend into the solvent bottle.

* * * * *